United States Patent
Kim et al.

(10) Patent No.: US 10,731,026 B2
(45) Date of Patent: Aug. 4, 2020

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 4 days.

(21) Appl. No.: 16/076,644

(22) PCT Filed: Sep. 5, 2017

(86) PCT No.: PCT/KR2017/009681
§ 371 (c)(1),
(2) Date: Aug. 8, 2018

(87) PCT Pub. No.: WO2018/048170
PCT Pub. Date: Mar. 15, 2018

(65) Prior Publication Data
US 2019/0047938 A1    Feb. 14, 2019

(30) Foreign Application Priority Data

Sep. 7, 2016 (KR) .................. 10-2016-0115271

(51) Int. Cl.
| | | |
|---|---|---|
| *C08K 5/12* | (2006.01) | |
| *C07C 69/82* | (2006.01) | |
| *C08K 5/00* | (2006.01) | |
| *C08K 5/10* | (2006.01) | |
| *C08L 23/06* | (2006.01) | |
| *C08L 23/12* | (2006.01) | |
| *C08L 25/06* | (2006.01) | |
| *C08L 27/06* | (2006.01) | |
| *C08L 61/02* | (2006.01) | |
| *C08L 75/04* | (2006.01) | |
| *C07C 67/08* | (2006.01) | |
| *C07C 69/75* | (2006.01) | |
| *C08L 23/08* | (2006.01) | |

(52) U.S. Cl.
CPC ............ *C08K 5/12* (2013.01); *C07C 67/08* (2013.01); *C07C 69/75* (2013.01); *C07C 69/82* (2013.01); *C08K 5/00* (2013.01); *C08K 5/0016* (2013.01); *C08K 5/10* (2013.01); *C08L 23/06* (2013.01); *C08L 23/0853* (2013.01); *C08L 23/12* (2013.01); *C08L 25/06* (2013.01); *C08L 27/06* (2013.01); *C08L 61/02* (2013.01); *C08L 75/04* (2013.01)

(58) Field of Classification Search
USPC .................................................. 524/285, 297
See application file for complete search history.

(56) References Cited

U.S. PATENT DOCUMENTS

| | | | |
|---|---|---|---|
| 10,030,119 | B2 | 7/2018 | Gourdin et al. |
| 10,544,279 | B2 | 1/2020 | Boeck et al. |
| 2013/0317152 | A1 | 11/2013 | Becker et al. |
| 2016/0237244 | A1 | 8/2016 | Boeck et al. |
| 2016/0326346 | A1 | 11/2016 | Gourdin et al. |

FOREIGN PATENT DOCUMENTS

| | | | | |
|---|---|---|---|---|
| EP | 2810982 | A1 | 12/2014 | |
| JP | 2015-217608 | A | 12/2015 | |
| JP | 2015-223700 | A | 12/2015 | |
| JP | 2016-74876 | A | 5/2016 | |
| KR | 10-0868194 | B1 | 11/2008 | |
| KR | 10-2009-0038514 | A | 4/2009 | |
| KR | 10-1264148 | B1 | 5/2013 | |
| KR | 10-2014-0005908 | A | 1/2014 | |
| KR | 10-2016-0101880 | A | 8/2016 | |
| WO | WO 2008/140177 | A1 * | 11/2008 | .............. C08L 31/08 |
| WO | 2014/195055 | A1 | 12/2014 | |
| WO | 2014/195056 | A1 | 12/2014 | |
| WO | 2015/101569 | A1 | 7/2015 | |

OTHER PUBLICATIONS

Online translation of Detailed Description of JP 2015-223700; publication date: Dec. 2015. (Year: 2015).*
Online translation of Detailed Description of KR 10-2009-0038514 (A); publication date: Apr. 2009 (Year: 2009).*

(Continued)

*Primary Examiner* — Fred M Teskin
(74) *Attorney, Agent, or Firm* — Dentons US LLP

(57) ABSTRACT

The present invention relates to a plasticizer composition and a resin composition including the same, and can provide a plasticizer composition in which three types of terephthalate-based materials and three types of cyclohexane 1,4-diester-based materials are mixed, and by which environmental friendliness can be secured, mechanical properties such as tensile strength and an elongation rate, physical properties such as migration properties and volatile loss can be improved to levels equal to or higher than those of existing products, and effects of improving processability and plasticizing efficiency can be expected, and a resin composition including the same.

8 Claims, No Drawings

(56) References Cited

OTHER PUBLICATIONS

Database WPI: "Industrial-material sheet made of soft polyvinylchloride resin for e.g. canvas comprises flexible laminated body by which soft-polyvinylchloride-resin layer is provided on surface by using fiber fabric as base material", XP002786238, Thomson Scientific, Dec. 14, 2015 (Corresponds to JP2015-223700A).

Database WPI: "Industrial sheet made of soft PVC resin for e.g. truck hood covers comprises flexible laminated body containing soft PVC resin layer provided on surface of fiber fabric as base material", XP002786239, Thomson Scientific, Dec. 7, 2015 (Corresponds to JP2015-217608A).

\* cited by examiner

PLASTICIZER COMPOSITION AND RESIN COMPOSITION INCLUDING THE SAME

CROSS-REFERENCE TO RELATED APPLICATION

This application is a National Stage Application of International Application No. PCT/KR2017/009681 filed Sep. 5, 2017, and claims the benefit of Korean Patent Application No. 10-2016-0115271 filed Sep. 7, 2016, all of which are hereby incorporated by reference in their entirety for all purposes as if fully set forth herein.

TECHNICAL FIELD

The present invention relates to a plasticizer composition including a mixture of three types of terephthalate-based materials and a mixture of three types of cyclohexane 1,4-diester-based materials, and a resin composition including the same.

BACKGROUND ART

In general, an alcohol reacts with a polycarboxylic acid such as phthalic acid and adipic acid to form the corresponding ester in a plasticizer. Further, studies on plasticizer compositions capable of replacing phthalate plasticizers such as terephthalate-based, adipate-based, and other high-molecular-weight plasticizers have been continued in consideration of domestic and foreign regulations of phthalate plasticizers harmful to humans.

Further, there is a growing demand for the eco-friendly products in a plastisol industry such as flooring, wallpaper, soft and hard sheets and the like, a calendaring industry, and extrusion/injection compound industries. In order to enhance quality characteristics, processability and productivity of the finished product, it is necessary to use a suitable plasticizer in consideration of discoloration, migration properties, mechanical properties, etc.

Various supplementary materials such as plasticizers, fillers, stabilizers, viscosity reducing agents, dispersants, antifoaming agents, foaming agents and the like are added depending on the characteristics required by industry in the various areas of use, such as tensile strength, an elongation rate, light resistance, migration properties, gelling properties, an absorption rate, etc.

For example, among the plasticizer compositions applicable to PVC, when di(2-ethylhexyl) terephthalate, which is most commonly used at relatively low cost, is applied, hardness or sol viscosity is high, the absorption rate of the plasticizer is relatively slow, and migration properties and stress migration properties are poor.

A hydrogenated material of di(2-ethylhexyl) terephthalate may be considered as a solution for this problem, but migration properties and thermal stability are poor while plasticizing efficiency is improved, and manufacturing costs are increased due to the hydrogenation reaction, so that it is difficult to achieve economic efficiency.

In order to address the above-described issues, there is a continuing need for the development of new composition products including a material superior in physical properties to di(2-ethylhexyl) 1,4-cyclohexanoate which is the hydrogenated di(2-ethylhexyl) terephthalate, or a novel derivative thereof, and studies on the development of products and applications of a vinyl chloride-based resin as an environmentally friendly plasticizer have been continued.

DISCLOSURE

Technical Problem

The present invention is directed to providing a plasticizer composition capable of improving poor physical properties caused by structural limitations, that is, a plasticizer composition which is eco-friendly, and has mechanical properties such as tensile strength and an elongation rate, physical properties such as migration properties, stress migration properties and volatile loss improved to levels equal to or higher than those of conventional products, and has improved processability and plasticizing efficiency.

Technical Solution

In order to achieve the above-described objective, according to an aspect of the present invention, there is provided a plasticizer composition, including: a terephthalate-based material including three types of compounds represented by the following Formula 1; and a cyclohexane 1,4-diester-based material including three types of compounds represented by the following Formula 2, where a weight ratio of the terephthalate-based material to the cyclohexane 1,4-diester-based material is in a range of 99:1 to 1:99.

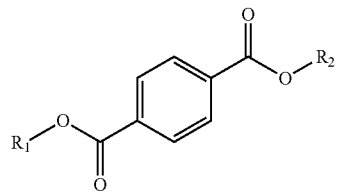

[Formula 1]

In Formula 1, $R_1$ and $R_2$ each independently represent an alkyl group having 4 to 10 carbon atoms.

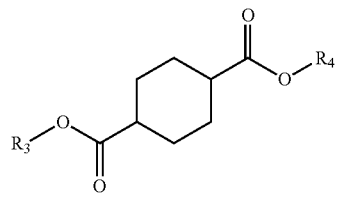

[Formula 2]

In Formula 2, $R_3$ and $R_4$ each independently represent an alkyl group having 4 to 10 carbon atoms.

In order to achieve the above-described objective, according to another aspect of the present invention, there is provided a resin composition including a resin at 100 parts by weight; and the above-described plasticizer composition at 5 to 150 parts by weight.

The resin may be one or more selected from the group consisting of ethylene vinyl acetate, polyethylene, polypropylene, polyketone, polyvinyl chloride, polystyrene, polyurethane and a thermoplastic elastomer.

Advantageous Effects

When a plasticizer composition according to an embodiment of the present invention is used in a resin composition, environment friendliness can be secured, mechanical properties such as tensile strength and an elongation rate, physical properties such as migration properties and volatile loss can be improved to levels equal to or higher than those of existing products, and effects of improving processability and plasticizing efficiency can be expected.

BEST MODE OF THE INVENTION

Hereinafter, the present invention will be described in detail in order to facilitate understanding of the present invention.

It should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

According to the present invention, a plasticizer composition includes a terephthalate-based material and a cyclohexane 1,4-diester-based material.

The terephthalate-based material may include three types of compounds represented by the following Formula 1.

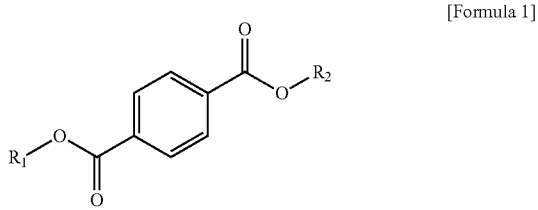

[Formula 1]

In Formula 1, $R_1$ and $R_2$ each independently represent an alkyl group having 4 to 10 carbon atoms.

Further, the cyclohexane 1,4-diester-based material may include three types of compounds represented by the following Formula 2.

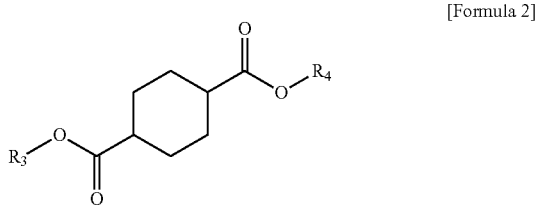

[Formula 2]

In Formula 2, $R_3$ and $R_4$ each independently represent an alkyl group having 4 to 10 carbon atoms.

In each of the terephthalate-based material and the cyclohexane 1,4-diester-based material included in the plasticizer composition, two types of compounds having the same substituents at the ends thereof and one type of compound having different substituents at the ends thereof may be included.

In the present specification, the terephthalate and cyclohexane 1,4-diesters having the same terminal substituents may be referred to as a "non-hybrid type" and the terephthalate and cyclohexane 1,4-diesters having different terminal substituents may be referred to as a "hybrid type."

In the present specification, for example, when $R_3$ and $R_4$ are the same, the cyclohexane 1,4-diester-based material may refer to dialkyl cyclohexane-1,4-diester, and when $R_3$ and $R_4$ are different, the cyclohexane 1,4-diester-based material may refer to alkyl ($R_3$) alkyl ($R_4$) cyclohexane-1,4-diester.

In Formulas 1 and 2, $R_1$ to $R_4$ may each be independently the same or different, and may be an alkyl group having 4 to 10 carbon atoms, and preferably, may be branched. Specifically, $R_1$ to $R_4$ may each independently represent an n-butyl group, an isobutyl group, an amyl group, a 2-ethylhexyl group, an isononyl group, an isodecyl group or a 2-propylheptyl group.

Further, when a terephthalate-based material and a cyclohexane 1,4-diester-based material which is a hydrogenated material of the terephthalate-based material are used together as in the plasticizer composition according to the present invention, there is a need to improve migration properties and thermal stability deteriorated due to hydrogenation, and it is required to maintain excellent properties such as tensile strength, an elongation rate, stress migration properties and volatile loss as well as improve migration properties and thermal stability by a terephthalate-based material mixed to reduce manufacturing costs increased due to hydrogenation.

However, di(2-ethylhexyl) cyclohexane-1,4-diester which is a hydrogenated material of the di(2-ethylhexyl) terephthalate is mixed and used as a method of improving processability, plasticizing efficiency and mechanical properties of commonly used di(2-ethylhexyl) terephthalate to which an alkyl group having 8 carbon atoms is bonded, and in this case, although processability and plasticizing efficiency can be improved, excellent tensile strength, an elongation rate, low volatile loss characteristics at an excellent level and migration loss of di (2-ethylhexyl) terephthalate are deteriorated, and thus it is difficult to say that the improvement is achieved in terms of overall plasticizer products.

In view of the problems as described above, in the present invention, the above-described physical properties can be improved by limiting the terephthalate-based material and cyclohexane 1,4-diester-based material to be mixtures of three types.

Specifically, when a plasticizer composition is prepared by mixing the terephthalate-based material and the cyclohexane 1,4-diester-based material which is the hydrogenated material of the terephthalate-based material, in which each of the materials includes a mixture of three types of compounds, that is, a mixture of two non-hybrid types of compound and one hybrid type of compound, the tensile strength and elongation rate can be further improved, and the migration loss and volatile loss can be improved without a large loss in processability and plasticizing efficiency.

More preferably, the terephthalate-based material includes three types of compounds represented by Formula 1, and when each of the compounds is referred to as compound A, compound B and compound C, in the order of each of A, B and C, mixed compositions such as 1) dibutyl terephthalate (DBTP), butyl(2-ethylhexyl) terephthalate (BEHTP) and di(2-ethylhexyl) terephthalate (DEHTP); 2) diisononyl terephthalate (DINTP), isononyl(2-ethylhexyl) terephthalate (INEHTP) and di(2-ethylhexyl) terephthalate (DEHTP); 3) dibutyl terephthalate (DBTP), butyl isononyl terephthalate (BINTP) and diisononyl terephthalate (DINTP); 4) di(2-propylheptyl) terephthalate (DPHTP) and (2-propylheptyl)(2-ethylhexyl) terephthalate (PHEHTP) and di(2-ethylhexyl) terephthalate (DEHTP); or 5) diamyl terephthalate (DATP), amyl isononyl terephthalate (AINTP) and diisononyl terephthalate (DINTP) may be used.

Further, the cyclohexane 1,4-diester-based material includes three types of compounds represented by Formula 2, and when each of the compounds is referred to as compound a, compound b and compound c, in the order of each of a, b and c, mixtures such as 1) dibutylcyclohexane-1,4-diester (1,4-DBCH), butyl(2-ethylhexyl) cyclohexane-1,4-diester (1,4-BEHCH) and di(2-ethylhexyl) cyclohexane-1,4-diester (1,4-DEHCH); 2) diisononyl cyclohexane-1,4-diester (1,4-DBCH), isononyl (2-ethylhexyl) cyclohexane-1,4-diester (1,4-BEHCH) and di(2-ethylhexyl) cyclohexane-1,4-diester (DEHCH); 3) dibutylcyclohexane-1,4-diester (1,4-DBCH), butyl isononyl cyclohexane-1,4-diester (1,4-BINCH) and diisononyl cyclohexane-1,4-diester (1,4-DINCH); 4) di(2-propylheptyl) cyclohexane-1,4-diester (1,4-DPHCH), (2-propylheptyl)(2-ethylhexyl) cyclohexane-1,4-diester (1,4-PHEHCH) and di(2-ethylhexyl) cyclohexane-1,4-diester (1,4-DEHCH); or 5) diamyl cyclohexane-1,4-diester (1,4-DACH), amyl isononyl cyclohexane-1,4-diester (1,4-AINCH) and diisononyl cyclohexane-1,4-diester (1,4-DINCH) may be used.

Here, "butyl" may be n-butyl or isobutyl.

Specifically, the above-described mixtures may have a specific composition ratio, and the composition ratio of each mixture component of both of the terephthalate-based material and the cyclohexane 1,4-diester-based material may be respectively 3.0 to 99.0 mol %; 0.5 to 96.5 mol % and 0.5 to 96.5 mol % in the order described above. The weight ratio thereof may be, preferably, in the range of 0.5 to 30 wt %; 10 to 50 wt %; and 40 to 89 wt %, respectively.

The composition ratio may be a mixed composition ratio generated by the esterification reaction, and may be an intended composition ratio by additionally mixing specific compounds, and the mixed composition ratio may be suitably adjusted according to the desired physical properties.

According to an embodiment of the present invention, the terephthalate-based material and cyclohexane 1,4-diester-based material may be included in a weight ratio of 99:1 to 1:99 in the plasticizer composition, and the upper limit of the ratio may be 99:1, and preferably 95:5, 90:10, 80:20 or 70:30, and the lower limit of the ratio may be 1:99, and preferably 30:70, or 40:60, and may be 50:50 or 60:40. Specifically, the weight ratio may be controlled from 99:1 to 1:99, 95:5 to 10:90, 90:10 to 10:90, 90:10 to 30:70 or 80:20 to 30:70.

When the terephthalate-based material and cyclohexane 1,4-diester-based material are mixed and used in the plasticizer composition as in the present invention, a plasticizer having excellent mechanical properties such as tensile strength and an elongation rate can be secured, the thermal stability, stress migration properties, migration properties, volatility characteristics such as volatile loss and the like can be improved, and the effect of processability and plasticizing efficiency can be maximized when a cyclohexane 1,4-diester compound is used at the same time.

Further, the plasticizer composition according to the present invention may not include a phthalate-based material. Generally, although the phthalate-based material has been used as a plasticizer that exhibits excellent physical properties, the phthalate-based material is classified as a substance that adversely affects the environment and the use thereof is limited. However, among the phthalate-based materials, while dioctyl phthalate (DOP) is registered as an environmentally regulated substance and the use thereof is extremely limited, diisononyl phthalate (DINP) or diisodecyl phthalate (DIDP) may be used in resin products which are not in contact with the human body depending on the use.

However, since the above-described phthalate-based material may not only cause environmental problems but also adversely affect the absorption rate of the plasticizer, and has a high possibility of adversely affecting migration properties, volatile loss and elongation rate characteristics, it is preferable that a phthalate-based material is not included in the plasticizer. Specifically, a phthalate-based material is generally not included in the plasticizer mainly used for eco-friendly products such as the above-described plasticizer composition.

According to an embodiment of the present invention, there is provided a method of preparing a plasticizer composition including: preparing a terephthalate-based material including a compound represented by the following Formula 1; preparing a cyclohexane 1,4-diester-based material including a compound represented by the following Formula 2 by performing a hydrogenation reaction of the terephthalate-based material in the presence of a metal catalyst; and blending the prepared terephthalate-based material with the hydrogenated cyclohexane 1,4-diester-based material.

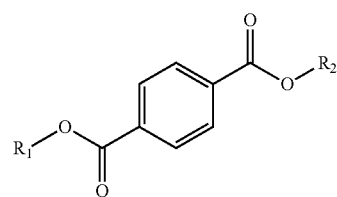

[Formula 1]

In Formula 1, $R_1$ and $R_2$ each independently represent an alkyl group having 4 to 10 carbon atoms,

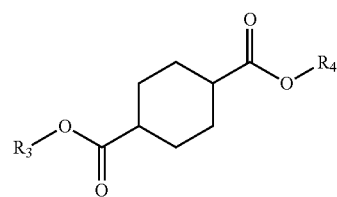

[Formula 2]

In Formula 2, $R_3$ and $R_4$ each independently represent an alkyl group having 4 to 10 carbon atoms.

The following preparation method is a method of preparing the above-described plasticizer composition, and has the same characteristics as that of the above-described plasticizer composition, unless specifically mentioned.

In the step of preparing the terephthalate-based material, the terephthalate-based material may be selectively prepared as a mixture, and the terephthalate-based material may be prepared by a direct esterification reaction in which terephthalic acid reacts with two types of alcohols selected from the group consisting of n-butyl alcohol, isobutyl alcohol, amyl alcohol, 2-ethylhexyl alcohol, isononyl alcohol, isodecyl alcohol and 2-propylheptyl alcohol.

The direct esterification reaction may be carried out by adding terephthalic acid to an alcohol and adding a catalyst thereto to perform a reaction under a nitrogen atmosphere; removing an unreacted alcohol and neutralizing an unreacted acid; and performing dehydration and filtration by vacuum distillation.

The alcohol may be used in an amount from 150 to 500 mol %, 200 to 400 mol %, 200 to 350 mol %, 250 to 400 mol % or 270 to 330 mol % based on 100 mol % of terephthalic acid.

Further, the catalyst, for example, may be selected one or more from acid catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid and alkyl sulfuric acid, metal salts such as aluminum lactate, lithium fluoride, potassium chloride, cesium chloride, calcium chloride, iron chloride and aluminum phosphate, metal oxides such as heteropolyacids, natural/synthetic zeolites, cation and anion exchange resins, and organometallic compounds such as tetraalkyltitanate and polymers thereof. As a specific example, tetraalkyltitanate may be used as the catalyst.

The amount of catalyst used may vary depending on the type, and an amount of the used catalyst is for example, for a homogeneous catalyst, 0.01 to 5 wt %, 0.01 to 3 wt %, 1 to 5 wt % or 2 to 4 wt % based on 100 wt % of the total reactants, for a heterogeneous catalyst, 5 to 200 wt %, 5 to 100 wt %, 20 to 200 wt %, or 20 to 150 wt % based on 100 wt % of the total reactants.

The direct esterification reaction is performed at a temperature range of 80 to 270° C., preferably 150 to 250° C. for 10 minutes to 10 hours, preferably for 30 minutes to 8 hours, and more preferably for 1 to 6 hours. Within the above-described temperature and time ranges, a terephthalate-based material may be effectively obtained.

Alternatively, the terephthalate-based material may be prepared by a transesterification reaction in which a terephthalate selected from dibutyl terephthalate, diamyl terephthalate, di(2-ethylhexyl) terephthalate, diisononyl terephthalate, diisodecyl terephthalate or di(2-propylheptyl) terephthalate reacts with an alcohol having an alkyl group different from an alkyl group of the terephthalate and selected from n-butyl alcohol, isobutyl alcohol, amyl alcohol, 2-ethylhexyl alcohol, isononyl alcohol, isodecyl alcohol and 2-propylheptyl alcohol.

The "transesterification reaction" used in the present invention refers to a reaction in which an alcohol reacts with an ester as shown in the following Reaction Formula 1 to exchange R" of an ester with R' of an alcohol as shown in the following Reaction Formula 1.

[Reaction Formula 1]

According to an embodiment of the present invention, when the transesterification reaction is carried out, three types of ester compositions may be generated in three cases including a case where an alkoxide of an alcohol attacks carbons of two ester (RCOOR") groups present in the ester-based compound; a case where the alkoxide of the alcohol attacks carbon of one ester (RCOOR") group present in the ester compound; and a case where a reaction is not performed.

Further, the transesterification reaction is advantageous in that wastewater problems are not caused as compared with an esterification reaction between acids and alcohols, and can proceed in the absence of a catalyst, thereby solving the problems in the use of an acid catalyst.

For example, a mixture of diisononyl terephthalate, isononyl (2-propylheptyl) terephthalate and di(2-propylheptyl) terephthalate may be generated by the transesterification reaction of diisononyl terephthalate with 2-propylheptyl alcohol, and the three types of terephthalates may be formed in an amount of 3.0 to 99.0 mol %; 0.5 to 96.5 mol % and 0.5 to 96.5 mol % based on the total molar amount of the mixture. Within the above-described range, there is an effect of obtaining a terephthalate-based material (mixture) having high process efficiency and excellent processability and an excellent absorption rate.

Further, the composition ratio of the mixture prepared by the transesterification reaction may be controlled according to the amount of the alcohol added.

The amount of the alcohol added may be in the range of 0.1 to 89.9 parts by weight, specifically 3 to 50 parts by weight, and more specifically 5 to 40 parts by weight based on 100 parts by weight of the terephthalate-based material. Further, the molar ratio of the terephthalate-based material and the alcohol may be preferably in the range of 1:0.005 to 5.0, 1:0.05 to 2.5, or 1:0.1 to 1.0. Within the above-described range, an ester-based plasticizer composition having high process efficiency and an excellent effect of improving processability can be obtained.

In the terephthalate-based material, the more the amount of alcohol added, the more the mole fraction of terephthalate participating in the transesterification reaction. Thus, the content of the two terephthalates as a product in the mixture may increase, and the unreacted content of terephthalate may correspondingly decrease.

However, the composition ratio of the mixture of the three types of terephthalates is not limited to the above-described range, and any one of the three types of terephthalates may be additionally added to change the composition ratio, and the mixed composition ratios which may be used are as described above.

The transesterification reaction may be performed at a reaction temperature of 120 to 190° C., preferably 135 to 180° C., and more preferably 141 to 179° C. for 10 minutes to 10 hours, preferably 30 minutes to 8 hours, and more preferably 1 to 6 hours. Within the above-described temperature and time ranges, a mixture which is a terephthalate-based material having a desired composition ratio can be effectively obtained. Here, the reaction time may be calculated from the point at which the temperature reaches the reaction temperature after the reactant is heated.

The transesterification reaction may be carried out in the absence of a catalyst, but in some cases, may be carried out in the presence of an acid catalyst or a metal catalyst, and in this case, the reaction time is shortened.

The acid catalyst may be, for example, sulfuric acid, methanesulfonic acid or p-toluenesulfonic acid, and the metal catalyst may be, for example, an organometallic catalyst, a metal oxide catalyst, a metal salt catalyst or a metal itself.

The metal component may be, for example, one or a mixture of two or more selected from the group consisting of tin, titanium and zirconium.

The hydrogenation reaction step may be a step of performing a hydrogenation reaction of the terephthalate-based material in the presence of a metal catalyst to partially convert the terephthalate-based material into the cyclohexane 1,4-diester-based material, thereby preparing the plasticizer composition in the form of a mixture.

As the terephthalate-based material used in the hydrogenation reaction, a material prepared in the step of preparing the terephthalate-based material may be used, or a commercially available terephthalate-based material may be purchased and used.

The reaction of the hydrogenation reaction step is a reaction for eliminating a double bond of a benzene ring of the terephthalate-based materials by adding hydrogen in the presence of a metal catalyst, and may be a kind of reduction reaction.

The hydrogenation reaction is for synthesizing the cyclohexane 1,4-diester-based material by carrying out a reaction of the terephthalate-based material with hydrogen in the presence of the metal catalyst, and the reaction conditions thereof may include all of the usual reaction conditions in which only the benzene ring can be hydrogenated without affecting a carbonyl group substituted in the benzene.

The hydrogenation reaction may be carried out by further including an organic solvent such as ethanol, but is not limited thereto. Examples of the metal catalyst include a Rh/C catalyst, a Pt catalyst, a Pd catalyst and the like which are generally used for hydrogenating the benzene ring, but are not limited thereto as long as the hydrogenation reaction as described above can be carried out.

Further, in the preparation of the cyclohexane 1,4-diester-based material, the cyclohexane 1,4-diester-based material may be prepared by a method of hydrogenating three types of terephthalate compositions having an alkyl group with 4 to 10 carbon atoms as described above, but may also be prepared by a transesterification reaction in which dimethyl cyclohexane-1,4-diester prepared by hydrogenating dimethyl terephthalate reacts with an alcohol having an alkyl group with 4 to 10 carbon atoms, followed by an additional transesterification reaction in which an alcohol of which the number of carbon atoms is different from that of the alcohol having an alkyl group with 4 to 10 carbon atoms and reacted with the dimethyl cyclohexane-1,4-diester, reacts with a cyclohexane-1,4-diester which is a reaction product of the preceding esterification reaction, or may be prepared by a direct esterification reaction in which cyclohexane-1,4-dicarboxylic acid prepared by hydrogenating terephthalic acid reacts with an alcohol having an alkyl group with 4 to 10 carbon atoms.

According to another embodiment of the present invention, there is provided a resin composition including the above-described plasticizer composition and the resin.

The resin may include known resins in the related field. For example, a mixture of at least one selected from the group consisting of ethylene vinyl acetate, polyethylene, polypropylene, polyvinyl chloride, polystyrene, polyurethane, a thermoplastic elastomer and polylactic acid may be used, but the resin is not limited thereto.

The plasticizer composition may be included at 5 to 150 parts by weight, preferably 5 to 100 parts by weight, or 10 to 70 parts by weight based on 100 parts by weight of the resin.

Generally, a resin in which the plasticizer composition is used may be manufactured into a resin product through melt processing or plastisol processing, and the melt-processed resin and the plastisol-processed resin may be produced differently depending on each polymerization method.

For example, when polyvinyl chloride is used for melt processing, since a resin is prepared by suspension polymerization, solid resin particles having a large average particle size are used. When polyvinyl chloride is used for plastisol processing, since a resin is prepared by emulsion polymerization or the like, a resin in a sol state is used as fine resin particles, and materials which act as fillers are generally further included in the plastisol processing.

The plasticizer composition according to the present invention may be suitable for the melt-processed resin, and when used in plastisol processing, migration properties and gelling properties may be deteriorated, thereby reducing processability and/or productivity. Thus, the plasticizer composition is preferably mixed with a resin used for melt processing. For example, the melt processing may be a processing method such as extrusion molding, injection molding, calendaring molding.

The resin composition may further include a filler. The filler may be included at 0 to 300 parts by weight, preferably, 50 to 200 parts by weight, and more preferably, 100 to 200 parts by weight based on 100 parts by weight of the resin.

The filler may include known fillers in the related field, and is not limited thereto. For example, the filler may be a mixture of at least one selected from the group consisting of silica, magnesium carbonate, calcium carbonate, calcium carbonate, hard coal, talc, magnesium hydroxide, titanium dioxide, magnesium oxide, calcium hydroxide, aluminum hydroxide, aluminum silicate, magnesium silicate and barium sulfate.

Further, the resin composition may further include another additive such as a stabilizer as necessary. The other additive such as the stabilizer may be included by 0 to 20 parts by weight, and preferably 1 to 15 parts by weight based on 100 parts by weight of the resin.

For example, the stabilizer may include a calcium-zinc (Ca—Zn)-based stabilizer such as calcium-zinc complex stearate, but is not limited thereto.

MODES OF THE INVENTION

Examples

Hereinafter, exemplary embodiments of the present invention will be described. However, the embodiments the present invention may be modified into a variety of different forms, and the scope of the present invention is not limited to the embodiments which will be described below. Further, the embodiments of the present invention are provided for the purpose of more fully describing the present invention to those skilled in the art.

Preparation Example 1: Preparation of Mixture of DEHTP/BEHTP/DBTP 2000 g of di(2-ethylhexyl) terephthalate (manufactured by LG Chemical Co., Ltd.) and 340 g of n-butanol (17 parts by weight based on 100 parts by weight of DEHTP) were charged into a reactor equipped with a stirrer, a condenser and a decanter, a transesterification reaction was carried out in a nitrogen atmosphere at a reaction temperature of 160° C. for 2 hours, and thereby a composition including dibutyl terephthalate (DBTP) at 4.0 wt %, butyl(2-ethylhexyl) terephthalate (BEHTP) at 35.0 wt % and di(2-ethylhexyl) terephthalate (DEHTP) at 61.0 wt % was prepared.

The reaction product was mixed and distilled to remove butanol and 2-ethylhexyl alcohol, and thereby a mixed composition was finally prepared.

Preparation Example 2: Preparation of Mixture of DINTP/EHINTP/DEHTP 498.0 g of purified terephthalic acid (PTA), 819 g of 2-ethylhexyl alcohol (2-EH) (the molar ratio of PTA:2-EH=1.0:2.1), 389 g of isononyl alcohol (INA)(the molar ratio of PTA:INA=1.0:0.9), and 1.54 g of a titanium-based catalyst (TIPT, tetra isopropyl titanate) (0.31 parts by weight based on 100 parts by weight of PTA) as a catalyst were added to a 3-liter four-neck reactor equipped with a cooler, a condenser, a decanter, a reflux pump, a temperature controller, a stirrer and the like, and a temperature was slowly raised to about 170° C. The generation of water was initiated at about 170° C., and an esterification reaction was conducted for about 4.5 hours while continuously introducing nitrogen gas at a reaction temperature of about 220° C. under atmospheric pressure. The reaction was terminated when an acid value reached 0.01.

After the completion of the reaction, distillation extraction was performed for 0.5 hours to 4 hours under reduced pressure in order to remove unreacted raw materials. Steam extraction was performed for 0.5 to 3 hours under reduced pressure using steam in order to remove the unreacted raw materials to below a predetermined content level. A temperature of a reaction solution was cooled to about 90° C. to perform a neutralization treatment using an alkaline solution. In addition, washing may be further performed and then water was removed by dehydrating the reaction solution. Filter media were introduced into the dehydrated reaction solution and stirred for a predetermined time. Then, the solution was filtered to finally obtain a composition including diisononyl terephthalate (DINTP) at 6 wt %, (2-ethylhexyl) isononyl terephthalate (EHINTP) at 30 wt % and di(2-ethylhexyl) terephthalate (DEHTP) at 64 wt %.

Preparation Example 3: Preparation of Hydrogenated Mixture of DEHTP/BEHTP/DBTP 1000 g of the composition prepared in Preparation Example 1 as a raw material and 20 g of a ruthenium catalyst (N.E CHEMCAT) were charged in a 1.5 L high-pressure reactor, hydrogen was added to a pressure of 8 MPa and a hydrogenation reaction was carried out at a temperature of 150° C. for 3 hours to complete the reaction. After completion of the reaction, the catalyst was filtered, and a mixed composition hydrogenated in a yield of 99% was prepared through a conventional purification process. Finally, a composition including di(2-ethylhexyl) cyclohexane 1,4-diester (1,4-DEHCH) at 55 wt %, butyl di(2-ethylhexyl) 1,4-cyclohexane diester (1,4-BEHCH) at 38 wt %, and dibutyl 1,4-cyclohexanediester (1,4-DBCH) at 7 wt % was obtained.

Preparation Example 4: Preparation of Hydrogenated Mixture of DINTP/EHINTP/DEHTP A hydrogenated mixed composition was finally obtained by hydrogenating the mixed composition in the same manner as in Preparation Example 3, except that the composition prepared in Preparation Example 2 was used instead of the composition prepared in Preparation Example 1. Finally, a composition including diisononyl cyclohexane 1,4-diester (1,4-DINCH) at 6 wt %, 2-ethylhexyl isononyl 1,4-cyclohexanediester (1,4-EHINCH) at 30 wt % and di(2-ethylhexyl) 1,4-cyclohexanediester(1,4-DEHCH) at 64 wt % was obtained.

Examples 1 to 4, Reference Example 1 and Comparative Examples 1 to 6: Mixed Plasticizer Composition Examples 1 to 4 were composed by using mixtures prepared by the method of sequentially applying the materials of Preparation Examples 1 to 4 and each of the preparation methods as shown in the following Table 1, and Reference Example 1 and Comparative Examples 1 to 6 were composed using di(2-ethylhexyl) terephthalate (DEHTP), dibutyl terephthalate (DBTP), di(2-ethylhexyl) cyclohexane-1,4-diester (purity: 99.5%)(1,4-DEHCH) and dibutylcyclohexane-1,4-diester (purity: 99.5%)(1,4-DBCH) manufactured by LG Chemical Co., Ltd. as shown in the following table.

TABLE 1

| | TP | Hydrogenated TP | Mixing ratio |
|---|---|---|---|
| Example 1 | Preparation Example 1 | Preparation Example 3 | 6:4 |
| Example 2 | Preparation Example 2 | Preparation Example 4 | 5:5 |
| Example 3 | Preparation Example 1 | Preparation Example 4 | 3:7 |
| Example 4 | Preparation Example 2 | Preparation Example 3 | 7:3 |
| Reference Example 1 | DEHTP | | |
| Comparative Example 1 | Preparation Example 1 | — | — |
| Comparative Example 2 | Preparation Example 2 | — | — |
| Comparative Example 3 | DEHTP | DEHCH | 5:5 |
| Comparative Example 4 | DBTP | DEHCH | 5:5 |
| Comparative Example 5 | DEHTP | DBCH | 5:5 |
| Comparative Example 6 | DBTP | DBCH | 7:3 |

DEHTP: di(2-ethylhexyl) terephthalate (LG Chemical Co., Ltd.)

Experimental Example 1: Evaluation of Physical Properties

Experimental specimens were prepared using the plasticizer compositions of the examples, reference example and comparative examples listed in Table 1 above.

In the preparation of the experimental specimens, 40 parts by weight of plasticizer compositions of Examples 1 to 4, Reference Example 1 and Comparative Examples 1 to 6, and 3 parts by weight of a stabilizer (BZ-153T) were mixed at 98° C. and 700 rpm in 100 parts by weight of PVC (LS100S) using a 3 L super mixer based on ASTM D638. A 5 mm sheet was prepared using a roll mill at 160° C. for 4 minutes. After performing pressing processes at 180° C. for 2.5 minutes at a low pressure and for 2 minutes at a high pressure, 1T and 3T sheets were prepared as specimens. The physical properties of each specimen were evaluated according to the following test items, and the results are summarized in the following Table 2.

<Test Items>
Hardness
Shore hardness (Shore "A" and Shore "D") 3T 10 s was measured at 25° C. in accordance with ASTM D2240.
Tensile Strength
A breaking point of a specimen was measured after pulling the specimen at a cross-head speed of 200 mm/min (1T) using a test instrument, U.T.M (model no; 4466, manufactured by Instron Corporation) according to the method of ASTM D638. The tensile strength was calculated as follows.

Tensile strength (kgf/mm$^2$)=Load value (kgf)/Thickness (mm)×width (mm)

Elongation Rate Measurement
A breaking point of a specimen was measured after pulling the specimen at a cross-head speed of 200 mm/min (1T) using the U.T.M according to the method of ASTM D638, and the elongation rate was calculated as follows.

Elongation rate (%)=Length after elongation/Initial length×100

Migration Loss Measurement

A specimen having a thickness of 2 mm or more was obtained in accordance with KSM-3156. Glass plates were attached to both sides of the specimen, and the load of 1 kgf/cm$^2$ was then applied thereto. The specimen was left standing for 72 hours in a hot air circulating oven (80° C.), and cooled at room temperature for 4 hours. Thereafter, the glass plates attached to both sides of the specimen were removed. Then, weights of the glass plates and specimen plate before and after being left standing in the oven were measured, and the migration loss was calculated by the following equation.

Migration loss (%)={(Initial weight of a specimen at room temperature−Weight of the specimen after being left standing in an oven)/Initial weight of the specimen at room temperature}×100

Volatile Loss Measurement

The specimen thus prepared was processed at 80° C. for 72 hours, and the weight of the specimen was measured.

Volatile loss (wt %)=(Initial weight of a specimen−Weight of the specimen after processing at 80° C. for 72 hours)/Initial weight of the specimen× 100

Absorption Rate Measurement

A resin and a plasticizer were mixed by using a planetary mixer (Brabender, P600) under mixing conditions of 77° C. and 60 rpm. The time period from mixing the resin and the plasticizer to obtaining a stabilized state of the torque of the mixer was measured and evaluated.

ticizer is absorbed too slowly, since the processing time may be delayed, not only the productivity of the whole process may be reduced, but also processability may be reduced because the temperature is required to increase during mixing. In the present invention, it may be evaluated that an absorption rate of about 4 minutes to 7 minutes and 30 seconds is excellent. Considering the application of the plasticizer composition, preferably, it may be evaluated that an absorption rate of about 4 minutes to 5 minutes and 30 seconds is excellent.

Referring to Table 2, it can be confirmed that, when the plasticizer composition in which the three types of terephthalate materials and the hydrogenated materials thereof were mixed was applied as in Examples 1 to 4, plasticizing efficiency (hardness) and processability (absorption rate) are improved, and not only mechanical properties such as tensile strength and an elongation rate but also volatile properties such as migration loss and volatile loss are improved as compared with those of Reference Example 1, which is a conventional plasticizer.

Further, it can be confirmed that the plasticizers of Examples 1 to 4 can have the physical properties of migration loss and volatile loss improved in a balanced manner, and the tensile strength and elongation rate are also improved to an acceptable level as compared with those of Comparative Examples 1 and 2 in which the terephthalate based material was not mixed with the hydrogenated material thereof and used alone.

In addition, it can confirmed that, in the case of mixed plasticizer compositions formed of single materials of Comparative Examples 3 to 6, the tensile strength and elongation

TABLE 2

|  | Hardness (Shore A) | Hardness (Shore D) | Tensile strength (kg/cm$^3$) | Elongation rate (%) | Migration loss (%) | Volatile loss (%) | Absorption rate (m:s) |
| --- | --- | --- | --- | --- | --- | --- | --- |
| Example 1 | 86.4 | 45.0 | 261.1 | 311.0 | 0.94 | 2.92 | 4:15 |
| Example 2 | 88.7 | 48.2 | 268.4 | 321.4 | 2.10 | 1.90 | 5:35 |
| Example 3 | 87.5 | 47.0 | 259.7 | 318.4 | 1.57 | 2.17 | 5:10 |
| Example 4 | 89.6 | 49.1 | 254.8 | 307.7 | 2.18 | 2.00 | 5:30 |
| Reference Example 1 | 90.7 | 50.2 | 227.9 | 279.6 | 2.57 | 2.64 | 6:15 |
| Comparative Example 1 | 87.3 | 47.6 | 252.9 | 305.2 | 1.81 | 4.10 | 4:30 |
| Comparative Example 2 | 91.4 | 51.0 | 241.0 | 268.2 | 3.11 | 1.32 | 7:35 |
| Comparative Example 3 | 87.0 | 47.5 | 215.7 | 265.0 | 3.56 | 5.64 | 5:30 |
| Comparative Example 4 | 82.3 | 42.5 | 187.6 | 235.4 | 8.58 | 17.85 | 3:27 |
| Comparative Example 5 | 84.4 | 43.6 | 209.8 | 238.0 | 6.80 | 12.56 | 4:15 |
| Comparative Example 6 | 80.1 | 40.5 | 165.4 | 240.2 | 14.30 | 20.35 | 2:30 |

Reference Example 1 is a representative commercial product which is a commercially available general plasticizer replacing the phthalate plasticizer, but does not satisfy both the plasticizing efficiency and processability, and is a typical example of a product requiring improvement in mechanical properties.

Further, for reference, the absorption rate represents the rate at which the plasticizer is absorbed into the resin, which is an indicator for confirming processability. For example, when the plasticizer is absorbed too quickly, it may adversely affect a process of processing the resin due to an increase in viscosity attributable to gelling and resin composition aggregation in the processing, and when the plasrate were significantly low, and volatile properties such as migration loss and volatile loss were also inferior, and although the level of the plasticizing efficiency (hardness) and processability (absorption rate) was similar to that of the examples, the physical properties were hardly improved since the poor physical properties are clearly seen from the viewpoint of the improvement of the overall physical properties.

In particular, in Comparative Examples 4 to 6, it was confirmed that volatile loss and migration loss were extremely poor since the values of volatile loss and migration loss were at least 10 times than those of examples. Also, it was confirmed that, in Comparative Examples 4 and 6, the tensile strength level was extremely low, and the absorption rate was too fast, and thus the gelling induction time was not secured.

While the present invention has been described in connection with exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A plasticizer composition, comprising:
   a terephthalate-based material including a mixture of three compounds represented by the following Formula 1; and
   a cyclohexane 1,4-diester-based material including a mixture of three compounds represented by the following Formula 2;
   wherein a weight ratio of the terephthalate-based material to the cyclohexane 1,4-diester-based material is in a range of 99:1 to 1:99:

[Formula 1]

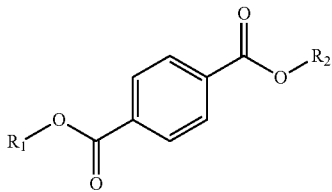

wherein in Formula 1, $R_1$ and $R_2$ each independently represent an alkyl group having 4 to 10 carbon atoms, and

[Formula 2]

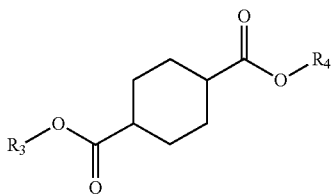

wherein in Formula 2, $R_3$ and $R_4$ each independently represent an alkyl group having 4 to 10 carbon atoms.

2. The plasticizer composition according to claim 1, wherein the weight ratio of the terephthalate-based material to the cyclohexane 1,4-diester-based material is in a range of 90:10 to 30:70.

3. The plasticizer composition according to claim 1, wherein the plasticizer composition does not include a phthalate-based material.

4. The plasticizer composition according to claim 1, wherein, in Formulas 1 and 2, $R_1$ to $R_4$ each are independently selected from the group consisting of an n-butyl group, an isobutyl group, a 2-ethylhexyl group, an isononyl group, an isodecyl group, and a 2-propylheptyl group.

5. The plasticizer composition according to claim 1, wherein the three compounds represented by Formula 1 are:
   1) dibutyl terephthalate (DBTP), butyl(2-ethylhexyl) terephthalate (BEHTP) and di(2-ethylhexyl) terephthalate (DEHTP);
   2) diisononyl terephthalate (DINTP), isononyl(2-ethylhexyl) terephthalate (INEHTP) and di(2-ethylhexyl) terephthalate (DEHTP);
   3) dibutyl terephthalate (DBTP), butyl isononyl terephthalate (BINTP) and diisononyl terephthalate (DINTP);
   4) di(2-propylheptyl) terephthalate (DPHTP) and (2-propylheptyl)(2-ethylhexyl) terephthalate (PHEHTP) and di(2-ethylhexyl) terephthalate (DEHTP); or
   5) diamyl terephthalate (DATP), amyl isononyl terephthalate (AINTP) and diisononyl terephthalate (DINTP).

6. The plasticizer composition according to claim 1, wherein the three compounds represented by Formula 2 are:
   1) dibutylcyclohexane-1,4-diester (1,4-DBCH), butyl(2-ethylhexyl) cyclohexane-1,4-diester (1,4-BEHCH) and di(2-ethylhexyl) cyclohexane-1,4-diester (1,4-DEHCH);
   2) diisononyl cyclohexane-1,4-diester (1,4-DBCH), isononyl (2-ethylhexyl) cyclohexane-1,4-diester (1,4-BEHCH) and di(2-ethylhexyl) cyclohexane-1,4-diester (DEHCH);
   3) dibutylcyclohexane-1,4-diester (1,4-DBCH), butyl isononyl cyclohexane-1,4-diester (1,4-BINCH) and diisononyl cyclohexane-1,4-diester (1,4-DINCH);
   4) di(2-propylheptyl) cyclohexane-1,4-diester (1,4-DPHCH), (2-propylheptyl)(2-ethylhexyl) cyclohexane-1,4-diester (1,4-PHEHCH) and di(2-ethylhexyl) cyclohexane-1,4-diester (1,4-DEHCH); or
   5) diamyl cyclohexane-1,4-diester (1,4-DACH), amyl isononyl cyclohexane-1,4-diester (1,4-AINCH) and diisononyl cyclohexane-1,4-diester (1,4-DINCH).

7. A resin composition, comprising a resin at 100 parts by weight;
   and the plasticizer composition according to claim 1 at 5 to 150 parts by weight.

8. The resin composition according to claim 7, wherein the resin is one or more selected from the group consisting of ethylene vinyl acetate, polyethylene, polypropylene, polyketone, polyvinyl chloride, polystyrene, polyurethane and a thermoplastic elastomer.

* * * * *